(12) United States Patent
ㅤㅤKhatibm

(10) Patent No.: US 8,067,171 B2
(45) Date of Patent: Nov. 29, 2011

(54) METHODS AND COMPOSITIONS FOR IMPROVED FERTILIZATION AND EMBRYONIC SURVIAL

(75) Inventor: Hasan Khatibm, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 156 days.

(21) Appl. No.: 12/424,796

(22) Filed: Apr. 16, 2009

(65) Prior Publication Data

US 2009/0299130 A1ㅤㅤDec. 3, 2009

Related U.S. Application Data

(60) Provisional application No. 61/046,253, filed on Apr. 18, 2008.

(51) Int. Cl.
ㅤㅤ*C12Q 1/68*ㅤㅤ(2006.01)
ㅤㅤ*C12P 19/34*ㅤㅤ(2006.01)
ㅤㅤ*C07H 21/02*ㅤㅤ(2006.01)

(52) U.S. Cl. ....... 435/6.1; 435/91.2; 536/23.1; 536/24.3

(58) Field of Classification Search ........................ None
ㅤㅤSee application file for complete search history.

(56) References Cited

U.S. PATENT DOCUMENTS

2010/0185047 A1*ㅤ7/2010ㅤKhatib ........................ 600/34

OTHER PUBLICATIONS

GenBank Locus NW_001495237, GI:119894208, 'Bos taurus chromosome 6 genomic contig, reference assembly', Dec. 22, 2006, from www.ncbi.nlm.nih.gov.*
Hacker UT et al. Gut (1997) vol. 40, pp. 623-627.*

* cited by examiner

*Primary Examiner* — Stephen Kapushoc
(74) *Attorney, Agent, or Firm* — Kening Li; Pinsent Masons LLP

(57) ABSTRACT

Single nucleotide polymorphic site at position 11646 of the bovine FGF2 gene is associated with improved fertilization rate and/or improved embryo survival rate, as well as improved milk production. Also disclosed are nucleic acid molecules, kits, methods of genotyping and marker assisted bovine breeding methods.

12 Claims, 1 Drawing Sheet

```
10321 agctttatga acagtatgtt taatcttatt gtagtcttat gaaagaagtg ttattttcat
10381 cttacagata gggatagagt ttttgctatt ggcttttcaa accatggtct ctttgtgatt
10441 gtaagtaatt aattgtgtct tccagatttg ttagtgttta gaatacagtt catggccaga
10501 atttcagatg gacggtgtgg cataaatttg aacagaaata gtgattttta aaaatagttt
10561 aaacttccca gagcctttac tgtgctcagc aaagttagtc tctcatcttt tcttctaccc
10621 ctttattgca tcctttttta tttagaaaat atttgtcatg aattaatacg aaacaattct
10681 ttaatatttt agggattgct ttctgaagaa ctcaaagatt tttaaaaggc atatttaaaa
10741 attaagagca ggacataatt aagaataaat accatataag aatgggataa acctcaaaga
10801 tagagtctgt aaagatgcag aataagctaa ggcatgcaga aaatacaaag agaatgatta
10861 aaaggatgtt taaaaagtta gttaggccct ttcaaggaaa tttgagatag gctcactatt
10921 taaggacata gtgtaagatg aaaagaaaaa aatttagaaa aaaaagcaga tggacctggg
10981 cctattttat gttaatgtta atcttcttct ccaagtgaga ttgtcaatca ataattgtct
11041 gagtgtctca ttgagaaaat aaagaccaag gtagacaaag agatacaaag aaagcactta
11101 gccagacaca tctagaaatg tgtttataat gaaactcctc tttccttgaa atcacttgtc
11161 cccctttttt gaccccctgt attttaaaat ataaatatt taactttgta aatttcttgc
11221 caaccagccc atctcgcaga gtacatttct actcttcatc ccctcagtct tcacatccgt
11281 ctcaggctct gtgttttcag ttctgctgtg tccttcatac tcacgggggt ctctgcattg
11341 ttgccacagc tgctctcgtt cggtccctga ctgttgcaac tgccttctac ctgatcccat
11401 ctgtatcagt ttgctagggc tgccataaca gattaccgta gactgagtgg ctcaaacaac
11461 agaaattgat tttctcatag ttctgtagac tagaagtcca agatacagct gtctgcatgt
11521 ctggtctttc tgcggcctct tcggggtttg cagcagccac cttacacatg gtcacctctc
11581 tgtgcacaca tcctgatctc ttcttcttgt aagggcacca ttcagatttg gttagggccc
11641 actctgtaac agccccattt tgacttaatc cttctttaga ggccccatct ccaaatagta
11701 attttctgag gtactggggc ttcaggcttc agtgtatgaa tttggggtgg gggtacagtt
11761 cagcccacag caccagtgag tcaactggat attgttcctt ggcagagtat ctttccagag
11821 agcagctctg atcttgttat ccctctattt agaaaaactt catggacagt ctagtcccct
11881 ggttcccaca ttgcttacag atgtgggcac tgtagaaagt ctatgagaat tacagagaat
11941 aggaagttac cagcagatga gtgattgtct tatatatcag aaagtgggat aaaggtattt
12001 tctggaaact ctagatagct aggaagcctg atgtaggtcc ttgaaaaaaa tccaagggac
12061 ttgagaatac ggagaaaaga agataacata gaaaatagta aataggctcg tatatagtgg
12121 aagagtagca gtatacatag gcttcacatg ttatttcggt ggaatatctg accaaatttc
12181 tcataacaac cttctgcaaa agaagtacat tttctttggg agagtagagt ttttttcatat
12241 ttgggcttct aaggccagga cccaaggact gtatcacctt taatgaactg gaagtatgct
12301 ctccctccaa aaggtaaaga attaaagata aaattggtga tatggattta ttatcatgat
12361 ctgaaagtat tcttaataga cagctgactc tgtttcctaa ttaccaccct gaagtgaagc
12421 tttagattct cattttaatt caaagctttt tgctagaccc ttcacccagc tattggcagt
12481 attgctcaca tcctcataca gcaggagaat ttttagtgat tacatgata ttttgcagct
12541 caacgaattt ttcttgaaag gcgttgcagg aagctacatt gctcaagaag tagatagtct
12601 tcaagtgttt taatgagatt aggaaaaaaa caccagttga gatacctgtt tggttatacc
12661 tctgttgagt cttttccaga cttgttattt tgggctgtac ttaatgatgt tgaactgtag
12721 agcttttgtg cataggattc tggagactct gggccttgcg catgccctca cctccagcag
12781 tgagagggtg ttcctactag gtacctctgt tttctggaag aagcctaatg ctcaccgtgg
12841 ctgacagtta atatatgtgg ttctttataa ttcagcctga ctcaaagaga tacagtacat
12901 cttccttcca ggttgggtat tttaacctgg acagtccatg aacaagctcc aggtttccat
12961 aattccttga aaatatatat aaaatattat atcaaggtgt tgtttctgag gggagaatac
13021 acagcacttt atcagattct caaaaagttg tccatggccc aaaatacgtc agggacactg
13081 ctgctgctaa ctgaggtgta tcttctcact aacccagctg tcgggaagag ccgatttgaa
13141 tgtgttgatt tgagtctgta gtttatggtg aatgatgctt gggagtaaca tctttgcaaa
13201 actggtgtct gtgttaattc taagaaatat ttcaagctgc tgttgatctc attacatagt
13261 gtccactctg aggcctcctg agggaaattt ctctgtggta actgtcggga ctagctcatg
13321 cttctccttg gcagccagtt tattttaacc ttatggactc tgggaagctt gttattgcta
13381 ctggcttcta gaaagcctaa tatgtggtcc acttctagca agtatgataa tctcaatcct
13441 ggcttcacaa attttaacc cttatttcct atttgcctta tttaaaacca ttttaaagt
13501 ttgtttttt gtcttggtat attgtctgta tctttgtaac tcatcttaaa tattatttgg
13561 ggccagacag gttacatacc tcaataaaaa attttattga tttcttattt taaccacaaa
```

Figure 1

SEQUENCE LISTING

<160> NUMBER OF SEQ ID NOS: 31

<210> SEQ ID NO 1
<211> LENGTH: 3300
<212> TYPE: DNA
<213> ORGANISM: Bos taurus

<400> SEQUENCE: 1

```
agctttatga acagtatgtt taatcttatt gtagtcttat gaaagaagtg ttattttcat      60
cttacagata gggatagagt ttttgctatt ggcttttcaa accatggtct ctttgtgatt     120
gtaagtaatt aattgtgtct tccagatttg ttagtgttta gaatacagtt catggccaga     180
atttcagatg gacggtgtgg cataaatttg aacagaaata gtgattttta aaaatagttt     240
aaacttccca gagcctttac tgtgctcagc aaagttagtc tctcatcttt tcttctaccc     300
ctttattgca tccttttta tttagaaaat atttgtcatg aattaatacg aaacaattct      360
ttaatatttt agggattgct ttctgaagaa ctcaaagatt tttaaaaggc atatttaaaa     420
attaagagca ggacataatt aagaataaat accatataag aatgggataa acctcaaaga     480
tagagtctgt aaagatgcag aataagctaa ggcatgcaga aaatacaaag agaatgatta     540
aaaggatgtt taaaaagtta gttaggccct ttcaaggaaa tttgagatag gctcactatt     600
taaggacata gtgtaagatg aaaagaaaaa aatttagaaa aaaaagcaga tggacctggg     660
cctatttat gttaatgtta atcttcttct ccaagtgaga ttgtcaatca ataattgtct      720
gagtgtctca ttgagaaaat aaagaccaag gtagacaaag agatacaaag aaagcactta     780
gccagacaca tctagaaatg tgtttataat gaaactcctc tttccttgaa atcacttgtc     840
cccctttttt gaccccctgt attttaaaat ataaatatt taactttgta aatttcttgc      900
caaccagccc atctcgcaga gtacatttct actcttcatc ccctcagtct tcacatccgt     960
ctcaggctct gtgttttcag ttctgctgtg tccttcatac tcacgggggt ctctgcattg    1020
ttgccacagc tgctctcgtt cggtccctga ctgttgcaac tgccttctac ctgatcccat    1080
ctgtatcagt ttgctagggc tgccataaca gattaccgta gactgagtgg ctcaaacaac    1140
agaaattgat tttctcatag ttctgtagac tagaagtcca agatacagct gtctgcatgt    1200
ctggtctttc tgcggcctct tcggggtttg cagcagccac cttacacatg gtcacctctc    1260
tgtgcacaca tcctgatctc ttcttcttgt aagggcacca ttcagatttg gttagggccc    1320
actctgtaac agccccattt tgacttaatc cttctttaga ggccccatct ccaaatagta    1380
attttctgag gtactggggc ttcaggcttc agtgtatgaa tttggggtgg gggtacagtt    1440
cagcccacag caccagtgag tcaactggat attgttcctt ggcagagtat cttteeagag    1500
agcagctctg atcttgttat ccctctattt agaaaaactt catggacagt ctagtcccct    1560
ggttcccaca ttgcttacag atgtgggcac tgtagaaagt ctatgagaat tacagagaat    1620
aggaagttac cagcagatga gtgattgtct tatatatcag aaagtgggat aaaggtattt    1680
tctggaaact ctagatagct aggaagcctg atgtaggtcc ttgaaaaaaa tccaagggac    1740
ttgagaatac ggagaaaaga agataacata gaaaatagta aataggctcg tatatagtgg    1800
aagagtagca gtatacatag gcttcacatg ttatttcggt ggaatatctg accaaatttc    1860
tcataacaac cttctgcaaa agaagtacat tttctttggg agagtagagt ttttcatat     1920
ttgggcttct aaggccagga cccaaggact gtatcacctt taatgaactg gaagtatgct    1980
ctccctccaa aaggtaaaga attaaagata aaattggtga tatggattta ttatcatgat    2040
```

-continued

```
ctgaaagtat tcttaataga cagctgactc tgtttcctaa ttaccaccct gaagtgaagc      2100
tttagattct cattttaatt caaagctttt tgctagaccc ttcacccagc tattggcagt      2160
attgctcaca tcctcataca gcaggagaat ttttagtgat ttacatgata ttttgcagct      2220
caacgaattt ttcttgaaag gcgttgcagg aagctacatt gctcaagaag tagatagtct      2280
tcaagtgttt taatgagatt aggaaaaaaa caccagttga gatacctgtt tggttatacc      2340
tctgttgagt cttttccaga cttgttattt tgggctgtac ttaatgatgt tgaactgtag      2400
agcttttgtg cataggattc tggagactct gggccttgcg catgccctca cctccagcag      2460
tgagagggtg ttcctactag gtacctctgt tttctggaag aagcctaatg ctcaccgtgg      2520
ctgacagtta atatatgtgg ttctttataa ttcagcctga ctcaaagaga tacagtacat      2580
cttccttcca ggttgggtat tttaacctgg acagtccatg aacaagctcc aggtttccat      2640
aattccttga aaatatatat aaaatattat atcaaggtgt tgtttctgag gggagaatac      2700
acagcacttt atcagattct caaaaagttg tccatggccc aaaatacgtc agggacactg      2760
ctgctgctaa ctgaggtgta tcttctcact aacccagctg tcgggaagag ccgatttgaa      2820
tgtgttgatt tgagtctgta gtttatggtg aatgatgctt gggagtaaca tctttgcaaa      2880
actggtgtct gtgttaattc taagaaatat ttcaagctgc tgttgatctc attacatagt      2940
gtccactctg aggcctcctg agggaaattt ctctgtggta actgtcggga ctagctcatg      3000
cttctccttg gcagccagtt tattttaacc ttatggactc tgggaagctt gttattgcta      3060
ctggcttcta gaaagcctaa tatgtggtcc acttctagca agtatgataa tctcaatcct      3120
ggcttcacaa attttaacc cttatttcct atttgcctta tttaaaacca tttttaaagt       3180
ttgttttttt gtcttggtat attgtctgta tctttgtaac tcatcttaaa tattatttgg      3240
ggccagacag gttacatacc tcaataaaaa attttattga tttcttattt taaccacaaa      3300
```

<210> SEQ ID NO 2
<211> LENGTH: 20
<212> TYPE: DNA
<213> ORGANISM: Artificial Sequence
<220> FEATURE:
<223> OTHER INFORMATION: PCR primer FGF2-1

<400> SEQUENCE: 2

```
gaaagctccg caatgtagag                                                  20
```

<210> SEQ ID NO 3
<211> LENGTH: 22
<212> TYPE: DNA
<213> ORGANISM: Artificial Sequence
<220> FEATURE:
<223> OTHER INFORMATION: PCR primer FGF2-2

<400> SEQUENCE: 3

```
ccaacaagga ccttttagtt gg                                               22
```

<210> SEQ ID NO 4
<211> LENGTH: 21
<212> TYPE: DNA
<213> ORGANISM: Artificial Sequence
<220> FEATURE:
<223> OTHER INFORMATION: PCR primer FGF2-3

<400> SEQUENCE: 4

```
gttaacaagg ccaagtggag g                                                21
```

```
<210> SEQ ID NO 5
<211> LENGTH: 19
<212> TYPE: DNA
<213> ORGANISM: Artificial Sequence
<220> FEATURE:
<223> OTHER INFORMATION: PCR primer FGF2-4

<400> SEQUENCE: 5
ctgcctcaca cgagctgtc                                              19

<210> SEQ ID NO 6
<211> LENGTH: 21
<212> TYPE: DNA
<213> ORGANISM: Artificial Sequence
<220> FEATURE:
<223> OTHER INFORMATION: PCR primer FGF2-5

<400> SEQUENCE: 6
ctgctcttcc aaggagatgt g                                           21

<210> SEQ ID NO 7
<211> LENGTH: 20
<212> TYPE: DNA
<213> ORGANISM: Artificial Sequence
<220> FEATURE:
<223> OTHER INFORMATION: PCR primer FGF2-6

<400> SEQUENCE: 7
ccaaactgag cagctcactg                                             20

<210> SEQ ID NO 8
<211> LENGTH: 20
<212> TYPE: DNA
<213> ORGANISM: Artificial Sequence
<220> FEATURE:
<223> OTHER INFORMATION: PCR primer FGF2-7

<400> SEQUENCE: 8
cagtgagctg ctcagtttgg                                             20

<210> SEQ ID NO 9
<211> LENGTH: 20
<212> TYPE: DNA
<213> ORGANISM: Artificial Sequence
<220> FEATURE:
<223> OTHER INFORMATION: PCR primer FGF2-8

<400> SEQUENCE: 9
cagatccctc ctgagtattc                                             20

<210> SEQ ID NO 10
<211> LENGTH: 22
<212> TYPE: DNA
<213> ORGANISM: Artificial Sequence
<220> FEATURE:
<223> OTHER INFORMATION: PCR primer FGF2-In1

<400> SEQUENCE: 10
tcagtcttca catccgtctc ag                                          22

<210> SEQ ID NO 11
<211> LENGTH: 21
<212> TYPE: DNA
<213> ORGANISM: Artificial Sequence
<220> FEATURE:
<223> OTHER INFORMATION: PCR primer FGF2-In2
```

```
<400> SEQUENCE: 11
tcatacactg aagcctgaag c                                              21

<210> SEQ ID NO 12
<211> LENGTH: 22
<212> TYPE: DNA
<213> ORGANISM: Artificial Sequence
<220> FEATURE:
<223> OTHER INFORMATION: PCR primer FGF2-In3

<400> SEQUENCE: 12
gaaccagtct gttgttccgt gt                                             22

<210> SEQ ID NO 13
<211> LENGTH: 23
<212> TYPE: DNA
<213> ORGANISM: Artificial Sequence
<220> FEATURE:
<223> OTHER INFORMATION: PCR primer FGF2-In4

<400> SEQUENCE: 13
cagatcagat cagatcagtc gct                                            23

<210> SEQ ID NO 14
<211> LENGTH: 20
<212> TYPE: DNA
<213> ORGANISM: Artificial Sequence
<220> FEATURE:
<223> OTHER INFORMATION: PCR primer FGF2-In5

<400> SEQUENCE: 14
gcatcaggtt tgaggatcaa                                                20

<210> SEQ ID NO 15
<211> LENGTH: 20
<212> TYPE: DNA
<213> ORGANISM: Artificial Sequence
<220> FEATURE:
<223> OTHER INFORMATION: PCR primer FGF2-In6

<400> SEQUENCE: 15
aggatcaagt tttccacctg                                                20

<210> SEQ ID NO 16
<211> LENGTH: 20
<212> TYPE: DNA
<213> ORGANISM: Artificial Sequence
<220> FEATURE:
<223> OTHER INFORMATION: PCR primer FGF2-In7

<400> SEQUENCE: 16
tcactcatgc ctggaagggt                                                20

<210> SEQ ID NO 17
<211> LENGTH: 21
<212> TYPE: DNA
<213> ORGANISM: Artificial Sequence
<220> FEATURE:
<223> OTHER INFORMATION: PCR primer FGF2-In8

<400> SEQUENCE: 17
tatgtccagg ttggcctata c                                              21

<210> SEQ ID NO 18
<211> LENGTH: 20
```

<212> TYPE: DNA
<213> ORGANISM: Artificial Sequence
<220> FEATURE:
<223> OTHER INFORMATION: PCR primer FGF2-In9

<400> SEQUENCE: 18
agagtctttc tctgagtcag                                              20

<210> SEQ ID NO 19
<211> LENGTH: 20
<212> TYPE: DNA
<213> ORGANISM: Artificial Sequence
<220> FEATURE:
<223> OTHER INFORMATION: PCR primer FGF2-In10

<400> SEQUENCE: 19
tgaagtcatt tggtgaaggc                                              20

<210> SEQ ID NO 20
<211> LENGTH: 21
<212> TYPE: DNA
<213> ORGANISM: Artificial Sequence
<220> FEATURE:
<223> OTHER INFORMATION: PCR primer FGF2-In11

<400> SEQUENCE: 20
cagcaactta gcactagcta c                                            21

<210> SEQ ID NO 21
<211> LENGTH: 20
<212> TYPE: DNA
<213> ORGANISM: Artificial Sequence
<220> FEATURE:
<223> OTHER INFORMATION: PCR primer FGF2-In12

<400> SEQUENCE: 21
cagaggctca ttacatggcc                                              20

<210> SEQ ID NO 22
<211> LENGTH: 20
<212> TYPE: DNA
<213> ORGANISM: Artificial Sequence
<220> FEATURE:
<223> OTHER INFORMATION: PCR primer FGF2-In13

<400> SEQUENCE: 22
atggtccagc tctcacatcc                                              20

<210> SEQ ID NO 23
<211> LENGTH: 21
<212> TYPE: DNA
<213> ORGANISM: Artificial Sequence
<220> FEATURE:
<223> OTHER INFORMATION: PCR primer FGF2-In14

<400> SEQUENCE: 23
gtgtaatatg tctgaaacat c                                            21

<210> SEQ ID NO 24
<211> LENGTH: 20
<212> TYPE: DNA
<213> ORGANISM: Artificial Sequence
<220> FEATURE:
<223> OTHER INFORMATION: PCR primer FGF2-In15

<400> SEQUENCE: 24
gctgatactg gtacattact                                              20

<210> SEQ ID NO 25
<211> LENGTH: 20
<212> TYPE: DNA
<213> ORGANISM: Artificial Sequence
<220> FEATURE:
<223> OTHER INFORMATION: PCR primer FGF2-In16

<400> SEQUENCE: 25
gcaaacagtg gctaccttgg                                         20

<210> SEQ ID NO 26
<211> LENGTH: 18
<212> TYPE: DNA
<213> ORGANISM: Artificial Sequence
<220> FEATURE:
<223> OTHER INFORMATION: PCR primer FGF2-In17

<400> SEQUENCE: 26
cctggtggct cagatggt                                           18

<210> SEQ ID NO 27
<211> LENGTH: 19
<212> TYPE: DNA
<213> ORGANISM: Artificial Sequence
<220> FEATURE:
<223> OTHER INFORMATION: PCR primer FGF2-In18

<400> SEQUENCE: 27
ctcagaattc tcatgcact                                          19

<210> SEQ ID NO 28
<211> LENGTH: 21
<212> TYPE: DNA
<213> ORGANISM: Artificial Sequence
<220> FEATURE:
<223> OTHER INFORMATION: PCR primer FGF2-F

<400> SEQUENCE: 28
catagttctg tagactagaa g                                       21

<210> SEQ ID NO 29
<211> LENGTH: 36
<212> TYPE: DNA
<213> ORGANISM: Artificial Sequence
<220> FEATURE:
<223> OTHER INFORMATION: PCR primer FGF2-R

<400> SEQUENCE: 29
cctctaaaga aggattaagt caaaatgggg ctggta                       36

<210> SEQ ID NO 30
<211> LENGTH: 20
<212> TYPE: DNA
<213> ORGANISM: Artificial Sequence
<220> FEATURE:
<223> OTHER INFORMATION: PCR primer FGF1-F

<400> SEQUENCE: 30
gacctattag atgtgacgcc                                         20

<210> SEQ ID NO 31
<211> LENGTH: 20
<212> TYPE: DNA
<213> ORGANISM: Artificial Sequence
<220> FEATURE:
<223> OTHER INFORMATION: PCR primer FGF1-R

```
<400> SEQUENCE: 31
ggactggctt tgctgagcag                                                    20
```

METHODS AND COMPOSITIONS FOR IMPROVED FERTILIZATION AND EMBRYONIC SURVIAL

CROSS REFERENCE TO RELATED APPLICATIONS

This application claims priority to U.S. patent application Ser. No. 61/046,253, filed on Apr. 18, 2009, the entire disclosure of which is incorporated hereby by reference.

STATEMENT OF GOVERNMENT INTEREST

This invention was made with United States government support awarded by the USDA under grant nos. USDA/CS-REES 09-CRHF-0-6055 and 07-CRHF-0-6055. The United States government has certain rights in this invention.

FIELD OF THE INVENTION

The present invention relates to a method of genetic testing for improved embryonic survival rate and mild production traits in cattle.

BACKGROUND OF THE INVENTION

At present, a major challenge of genomic and genetic studies in livestock species is the identification and mapping of individual quantitative trait loci (QTL) and quantitative trait genes (QTG) that control agricultural traits. Candidate genes are typically chosen based on the results of previous linkage mapping studies and on comparative biological or physiological functions in other species (Rothschild and Soller, 1997). A review of recent publications shows that many QTL have been mapped for traits of economical importance in dairy cattle (see e.g. Khatkar et al., 2004). However, despite the large number of QTL studies in cattle and other species, little progress has been made on the identification of major genes affecting milk production, fertility and health traits in dairy cattle. One major limitation when choosing a candidate gene is the large number of provisional genes present in most QTL regions.

Reproductive performance in high-producing dairy cows is currently suboptimal and continues to decline as characterized by low fertilization rates and reduced embryonic survival (Moore and Thatcher, 2006). The decrease in fertility in dairy cattle is a worldwide problem. In the U.S.A., the first-service conception rate has been decreasing for many years with an estimated decline of 0.45% per year over a 20-year period (Butler and Smith, 1989). Lucy (2001) estimated that the first-service conception rate had declined from about 65% in 1951 to 40% in 1996. In the U.K., the conception rate is declining at about 1% per year, and at first-service it is currently lower than 40% (Royal et al., 2000). The reasons for the reduced reproductive efficiency are manifold, but it seems likely that there are substantial genetic effects contributing to this infertility, despite the low heritability of most fertility traits (VeerKamp and Beerda, 2007). Shook (2006) estimated that genetics account for about one-third of the decrease in daughter pregnancy rates.

Despite the large number of quantitative trait loci studies in cattle and other species, little progress has been made on the identification of major genes affecting reproduction traits (Veerkamp and Beerda, 2007). The present inventors previously have identified single nucleotide polymorphisms (SNPs) that may be used to predict improved fertility in dairy cattle, including those located in the signal transducer and activator 5A (STATA), known to play an important role in cytokine signaling pathways. See e.g. Khatib et al., 2008.

Such major genes would facilitate genetic testing of bulls that enable quick and accurate evaluation of its fertility and the survival rate of embryos conceived from these bulls. Genetic testing of the bulls to determine their fertility and embryo survival rate can lower the high cost of the traditional, progeny testing methods, by by-passing the need to produce live birth.

In addition, identification of major genes that affect reproduction traits can facilitate marker-assisted selection, which can lower the high cost of progeny testing currently used to improve sires. With marker-assisted selection, young bull progeny could be evaluated immediately after birth or even before birth, and those young bulls that are determined by genetic testing to have undesirable markers would never be progeny tested, for the presence/absence of the marker.

The present disclosure provides such a genetic marker that can be used for genetic testing and for marker-assisted selection process.

SUMMARY OF THE INVENTION

The present inventor recognized the role of the fibroblast growth factor 2 (FGF2) gene in regulating trophectoderm expression of interferon-tau (IFNT), the maternal pregnancy recognition factor in ruminants (Ocon-Grove et al., 2007; Michael et al., 2006), and chose FGF2 to test for association with embryonic survival and fertilization rate. Bovine FGF2 has been mapped to chromosome 17, with 3 exons and a total length of over 55 kb. Also, it is expressed by the endometrium throughout the estrous cycle and early pregnancy (Michael et al., 2006).

The present inventor used the pooled DNA sequencing approach to identify SNPs in FGF2. Sequencing of a total of 6.4 kb including 3 exons of the gene revealed only one SNP (A/G): in intron 1 at position 11646. This position is hereinafter referred to as the "polymorphic site." This SNP, referred to as SNP11646, was investigated for association with production traits in individuals from Holstein populations: the granddaughter-design CDDR and the daughter-design UW populations from the U.S.A. FGF2 variants were found to associate with fat yield and percentage, Somatic cell score (SCS), and productive life with significant dominance and complete dominance effects. For the CDDR population, no significant associations were observed for the examined traits. Given that FGF2 was chosen for this study because of its role in the INFT signal transduction pathway and was found to be associated with production traits, the results suggest that the candidate pathway could be an attractive strategy to search for candidate quantitative trait genes.

The effect of FGF2 on fertility was also investigated. Specifically, in vitro fertilized embryos were produced from 281 Holstein cows and from 7 sires. A total of 4,542 in vitro fertilizations were performed, from which a total of 3,171 embryos were produced. Survival and fertilization rates were assessed at Day 7 of embryonic development. Using the pooled DNA sequencing approach, 2 SNPs were identified in FGF2, SNP11646 and SNP23. All sires and cows were genotyped for these SNPs, and SNP11646 was found to have a significant effect on survival rate. The survival rate of embryos produced from GG cows for this SNP was 37% vs. 28% and 29% for embryos produced from AG and AA cows, respectively. This disclosure provides the first evidence of association between FGF2 and embryonic mortality in cattle.

Based on the results summarized above, the present invention provides an isolated nucleic acid molecule comprising at least one polymorphic site selected from the group consisting of position of SEQ ID NO: 1 (the bovine FGF2 gene), and at least 8, 9, 10, 11, 12, 13, 14, 15, 16 or 17 contiguous nucleotides or bases of SEQ ID NO: 1 adjacent to the polymorphic site, wherein the nucleic acid molecule comprises a guanine at position 11646. It is recognized that SEQ ID NO: 1, wherein position 1326 is an A nucleotide, is already known, and the nucleic acid molecule therefore does not encompass one that consists of SEQ ID NO: 1 where position 1326 is an A nucleotide.

Preferably, the nucleic acid molecule which comprises at least 15, more preferably at least 20, still more preferably at least 25, contiguous bases of SEQ ID NO: 1 adjacent to the polymorphic site. In one embodiment, the isolated nucleic acid molecule comprises not more than 1,500 nt, preferably not more than 1000 nt, more preferably not more than 900 nt, more preferably not more than 800 nt, more preferably not more than 700 nt, preferably not more than 600 nt, more preferably not more than 500 nt, preferably not more than 400 nt, more preferably not more than 300 nt, more preferably not more than 150 nt., preferably not more than 100 nt., still more preferably not more than 50 nt.

The nucleic acid molecule preferably contains the polymorphic site which is within 4 nucleotides of the center of the nucleic acid molecule. Preferably, the polymorphic site is at the center of the nucleic acid molecule.

In another embodiment, the nucleic acid molecule contains the polymorphic site which is at the 3'-end of the nucleic acid molecule.

In another embodiment, the nucleic acid molecule contains the polymorphic site which is at the 5'-end of the nucleic acid molecule.

The present invention also provides an array of nucleic acid molecules comprising at least two nucleic acid molecules described above.

The present invention further provides a kit comprising a nucleic acid molecule described above, and a suitable container.

Also provided is a method for detecting SNPs in a bovine FGF2 gene, wherein the FGF2 gene has a nucleic acid sequence of SEQ ID NO: 1, the method comprising determining the identity of a nucleotide at position 11646, and comparing the identity to the nucleotide identity at a corresponding position of SEQ ID NO: 1.

In another embodiment, the present invention provides a method for genotyping a bovine cell, using the method above. Suitable bovine cell may be an adult cell, an embryo cell, a sperm, an egg, a fertilized egg, or a zygote. The identity of the nucleotide may be determined by sequencing the FGF2 gene, or a relevant fragment thereof, isolated from the cell.

In a further embodiment, the present invention provides a method for testing the fertility of a bull cattle, the method comprising collecting a nucleic acid sample from the cattle, and genotyping said nucleic sample as described above, wherein a bull having a FGF2 gene sequence which comprises a guanine at position 11646 is selected for breeding purposes.

Preferably, a bull having a FGF2 gene sequence which is homozygous at the above described polymorphic site is selected for breeding purposes.

Preferably, a bull having a FGF2 gene sequence which comprises a guanine at position 11646 is selected for breeding purposes.

Preferably, a bull having a FGF2 gene sequence which is homozygously G at position 11646 is selected for breeding purposes.

Further provided is a method for selectively breeding of cattle using a multiple ovulation and embryo transfer procedure (MOET), the method comprising superovulating a female animal, collecting eggs from said superovulated female, in vitro fertilizing said eggs from a suitable male animal, implanting said fertilized eggs into other females allowing for an embryo to develop, genotyping the developing embryo, and terminating pregnancy if the developing embryo does not have guanine (C) at position 11646. Preferably, pregnancy is terminated if the embryo is not homozygously G at position 11646.

In a preferred embodiment, the present invention provides a method for selectively breeding dairy cattles, comprising selecting a bull whose FGF2 gene is hemizygously or homozygously guanine at position 11646, and using its semen for fertilizing a female animal. Preferably the bull is homozygous with regard to the above SNP site. More preferably, the female animal is also homozygous at the above SNP site.

DESCRIPTION OF THE DRAWINGS

FIG. 1 shows the FGF2 gene sequence (SEQ ID NO: 1) where the polymorphic site at position 11646 is shown as shaded and bold.

DETAILED DESCRIPTION OF THE INVENTION

It has been found at least two positions of the bovine FGF2 gene are polymorphic. The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. Polymorphisms generally have at least two alleles, each occurring at a significant frequency in a selected population. A polymorphic locus may be as small as one base pair. The first identified allelic form is arbitrarily designated as the reference form, and other allelic forms are designated as alternative or variant alleles. The allelic form occurring most frequently in a selected population is sometimes referred to as the wild type form. Diploid organisms may be homozygous or heterozygous for allelic forms. A biallelic polymorphism has two forms, and a triallelic polymorphism has three forms, and so on.

Polymorphisms may provide functional differences in the genetic sequence, through changes in the encoded polypeptide, changes in mRNA stability, binding of transcriptional and translation factors to the DNA or RNA, and the like. Polymorphisms are also used to detect genetic linkage to phenotypic variation.

One type of polymorphism, single nucleotide polymorphisms (SNPs), has gained wide use for the detection of genetic linkage recently. SNPs are generally biallelic systems, that is, there are two alleles that an individual may have for any particular SNP marker. In the instant case, the SNPs are used for determining the genotypes of the FGF2 gene, which are found to have strong correlation to embryonic mortality rate.

It is to be understood that any nucleic sequence provided herein also encompasses the complementary sequence corresponding thereto. In order to provide an unambiguous identification of the specific site of a polymorphism, the numbering of the original FGF2 sequence in the GenBank is shown in FIG. 1 and is used throughout this disclosure.

The present invention provides nucleic acid based genetic markers for identifying bovine animals with superior breeding (such as fertility and embryo survival rates) traits. In general, for use as markers, nucleic acid fragments, preferably DNA fragments, may be as short as 7 nucleotides (nt), but may preferably be at least 12 nt, 15 nt, usually at least 20 nt, often at least 50 nt. Such small DNA fragments are useful as primers for the polymerase chain reaction (PCR), and probes for hybridization screening, etc.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nt. Short primer molecules generally require cooler temperatures to form sufficiently stable hybrid complexes with the template. A primer need not reflect the exact sequence of the template but must be sufficiently complementary to hybridize with a template. The term primer site, or priming site, refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

The term "probe" or "hybridization probe" denotes a defined nucleic acid segment (or nucleotide analog segment) which can be used to identify by hybridizing to a specific polynucleotide sequence present in samples, said nucleic acid segment comprising a nucleotide sequence complementary of the specific polynucleotide sequence to be identified. "Probes" or "hybridization probes" are nucleic acids capable of binding in a base-specific manner to a complementary strand of nucleic acid.

An objective of the present invention is to determine which embodiment of the polymorphisms a specific sample of DNA has. For example, it is desirable to determine whether the nucleotide at a particular position is A or G. An oligonucleotide probe can be used for such purpose. Preferably, the oligonucleotide probe will have a detectable label, and contains an A at the corresponding position. Experimental conditions can be chosen such that if the sample DNA contains an A, they hybridization signal can be detected because the probe hybridizes to the corresponding complementary DNA strand in the sample, while if the sample DNA contains a G, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, or RT-PCR amplification of the mRNA transcript of the FGF2 gene, or a suitable fragment thereof. The use of the polymerase chain reaction is described in Saiki et al. (1985) Science 230:1350-1354. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) Nucleic Acids Res. 18:2887-2890; and Delahunty et al (1996) Am. J. Hum. Genet. 58:1239-1246. The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or non-covalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other.

Hybridization may also be performed with nucleic acid arrays and subarrays such as described in WO 95/11995. The arrays would contain a battery of allele-specific oligonucleotides representing each of the polymorphic sites. One or both polymorphic forms may be present in the array, for example the polymorphism of position 11646 of the FGF2 gene may be represented by either, or both, of the listed nucleotides. Usually such an array will include at least 2 different polymorphic sequences, i.e. polymorphisms located at unique positions within the locus. Arrays of interest may further comprise sequences, including polymorphisms, of other genetic sequences, particularly other sequences of interest. The oligonucleotide sequence on the array will usually be at least about 12 nt in length, may be the length of the provided polymorphic sequences, or may extend into the flanking regions to generate fragments of 100 to 200 nt in length. For examples of arrays, see Ramsay (1998) Nat. Biotech. 16:4044; Hacia et al. (1996) Nature Genetics 14:441-447; Lockhart et al. (1 996) Nature Biotechnol. 14:1675-1680; and De Risi et al. (1996) Nature Genetics 14:457-460.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the *E. coli* mutS protein (Modrich, P. Ann. Rev. Genet. 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nucl. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruao et al., Nucl. Acids Res. 17:8392, 1989; Ruao et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO 89/10414).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $35S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

It is readily recognized by those ordinarily skilled in the art that in order to maximize the signal to noise ratio, in probe hybridization detection procedure, the polymorphic site should at the center of the probe fragment used, whereby a mismatch has a maximum effect on destabilizing the hybrid molecule; and in a PCR detection procedure, the polymorphic site should be placed at the very 3'-end of the primer, whereby a mismatch has the maximum effect on preventing a chain elongation reaction by the DNA polymerase. The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center," and so on.

In some embodiments, a composition contains two or more differently labeled oligonucleotides for simultaneously probing the identity of nucleotides or nucleotide pairs at two or more polymorphic sites. It is also contemplated that primer compositions may contain two or more sets of allele-specific primer pairs to allow simultaneous targeting and amplification of two or more regions containing a polymorphic site.

Alternatively, the relevant portion of the FGF2 gene of the sample of interest may be amplified via PCR and directly sequenced, and the sequence be compared to the wild type sequence shown in FIG. 1. It is readily recognized that, other than those specifically disclosed herein, numerous primers can be devised to achieve the objectives. PCR and sequencing techniques are well known in the art and reagents and equipments are readily available commercially.

DNA markers have several advantages; segregation is easy to measure and is unambiguous, and DNA markers are co-dominant, i.e., heterozygous and homozygous animals can be distinctively identified. Once a marker system is established, selection decisions could be made very easily, since DNA markers can be assayed any time after a blood sample can be collected from the individual infant animal, or even earlier by testing embryos in vitro if very early embryos are collected.

The use of marker assisted genetic selection will greatly facilitate and speed up cattle breeding problems. For example, a modification of the multiple ovulation and embryo transfer (MOET) procedure can be used with genetic marker technology. Specifically, females are superovulated, eggs are collected, in vitro fertilized using semen from superior males and implanted into other females allowing for use of the superior genetics of the female (as well as the male) without having to wait for her to give birth to one calf at a time. Developing blastomeres at the 4-8 cell stage may be assayed for presence of the marker, and selection decisions made accordingly.

In one embodiment of the invention an assay is provided for detection of presence of a desirable genotype using the markers.

The term "genotype" as used herein refers to the identity of the alleles present in an individual or a sample. In the context of the present invention, a genotype preferably refers to the description of the polymorphic alleles present in an individual or a sample. The term "genotyping" a sample or an individual for a polymorphic marker refers to determining the specific allele or the specific nucleotide carried by an individual at a polymorphic marker.

The present invention is suitable for identifying a bovine, including a young or adult bovine animal, an embryo, a semen sample, an egg, a fertilized egg, or a zygote, or other cell or tissue sample therefrom, to determine whether said bovine possesses the desired genotypes of the present invention, which are indicative of improved reproductive traits.

Further provided is a method for genotyping the bovine FGF2 gene, comprising determining for the two copies of the FGF2 gene present in the bovine the identity of the nucleotide pair at position 11646.

One embodiment of a genotyping method of the invention involves examining both copies of the FGF2 gene, or a fragment thereof, to identify the nucleotide pair at the polymorphic site in the two copies to assign a genotype to the individual. In some embodiments, "examining a gene" may include examining one or more of: DNA containing the gene, mRNA transcripts thereof, or cDNA copies thereof. As will be readily understood by the skilled artisan, the two "copies" of a gene, mRNA or cDNA, or fragment thereof in an individual may be the same allele or may be different alleles. In another embodiment, a genotyping method of the invention comprises determining the identity of the nucleotide pair at the polymorphic site.

The present invention further provides a kit for genotyping a bovine sample, the kit comprising in a container a nucleic acid molecule, as described above, designed for detecting the polymorphism, and optionally at least another component for carrying out such detection. Preferably, a kit comprises at least two oligonucleotides packaged in the same or separate containers. The kit may also contain other components such as hybridization buffer (where the oligonucleotides are to be used as a probe) packaged in a separate container. Alternatively, where the oligonucleotides are to be used to amplify a target region, the kit may contain, preferably packaged in separate containers, a polymerase and a reaction buffer optimized for primer extension mediated by the polymerase, such as PCR.

In one embodiment the present invention provides a breeding method whereby genotyping as described above is conducted on bovine embryos, and based on the results, certain cattle are either selected or dropped out of the breeding program.

Through use of the linked marker loci, procedures termed "marker assisted selection" (MAS) may be used for genetic improvement within a breeding nucleus; or "marker assisted introgression" for transferring useful alleles from a resource population to a breeding nucleus (Soller 1990; Soller 1994).

As summarized above, the present inventors recognized the role of the FGF2 gene in regulating trophectoderm expression of interferon-tau (IFNT), the maternal pregnancy recognition factor in ruminants, and choose FGF2 to test for association with embryonic survival and fertilization rate. The inventors produced a total of 4,542 in vitro fertilizations, resulting in a total of 3,171 embryos. Survival and fertilization rates were assessed at Day 7 of embryonic development. Using the pooled DNA sequencing approach, 2 single nucleotide polymorphisms (SNP) were identified in FGF2, SNP11646 and SNP23. All sires and cows were genotyped for these SNP, and SNP11646 was found to have a significant effect on survival rate. The survival rate of embryos produced from GG cows for this SNP was 37% vs. 28% and 29% for embryos produced from AG and AA cows, respectively.

The present inventors used the pooled DNA sequencing approach to find polymorphisms in more than 6 kb of FGF2 including all the exons and the 3' UTR, and found only one SNP at position 23 (SNP23) and one SNP in intron 1 (SNP11646).

The identification of genes causing early embryonic death is a challenging task in mammalian species (VanRaden and Miller, 2006). Successful discovery of such genes requires both the development of an appropriate resource population and an appropriate strategy of choosing candidate genes. The present study met both of these requirements in an investigation of the association between FGF2 polymorphisms and survival rate and fertilization success. First, we have collected ovaries from cows whose oocytes have been used to generate IVF embryos with the aim of identifying genes affecting fertility traits in cattle. Second, FGF2 was chosen as a candidate gene affecting early embryonic survival because of its roles in embryonic development and in the signal transduction pathway of IFNT, which has a key role in the initiation and maintenance of pregnancy in ruminants (Spencer and Bazer, 2004). Using the same dataset, we previously showed that mutations in signal transducer and activator 5A (STAT5A) are associated with embryonic survival, fertilization rate, and milk composition in Holstein dairy cattle (Khatib et al., 2008). It is worth noting that STAT5A is also a member of IFNT signal transduction pathway.

Although the mechanisms that cause embryonic mortality have not yet been identified, several studies have reported the important role of FGF2 in early stages of embryo development and initiation of pregnancy. The present inventor herein provides the first evidence of the involvement of FGF2 in embryonic mortality in cattle. Larson et al. (1992) reported that the addition of the growth factors FGF2 and transforming growth factor beta to cultures of IVF embryos improved the development of these embryos to blastocyst stages. Carlone and Rider (1993) have shown that the uterine expression of FGF2 was increased by the implanting embryo in rats. Moreover, they showed that in the presence of the embryo, FGF2 was expressed by the endometrium both intra- and extracellularly, while in the absence of the embryo, FGF2 expression differed significantly. The authors suggested that intra- and extracellular FGF2 has a role in the cellular communication between the embryo and the uterus and that the developing embryos may employ the maternal growth factors for their own development (Carlone and Rider, 1993). More recently, Michael and colleagues (2006) reported that FGF2 is expressed in the endometrium throughout the estrous cycle and that this gene controls the expression of IFNT. Given that IFNT plays a key role in regulating the expression of genes involved in embryo implantation and in protection of the conceptus against maternal rejection (Martal et al., 1997), the instant disclosure that FGF2 is associated with early embryonic death is in agreement with the exciting discovery of Michael and colleagues (2006).

The present inventor previously has shown that other members of the IFNT pathway—osteopontin, STAT1, uterine milk protein—are also associated with milk production and health traits (Leonard et al. 2005; Cobanoglu et al., 2006; Khatib et al., 2007a; Khatib et al., 2007b). Here it is disclosed that the GG genotype of FGF2 SNP11646 is associated with significant increases in milk composition and productive life in Holstein dairy cattle populations. It is also disclosed that the A allele was associated with a significant decrease in embryonic survival. Thus, the findings on the involvement of STAT5A and FGF2 in both milk production and fertility traits imply that IFNT pathway could be an excellent candidate pathway to search for other genes that tie milk production and health traits of cows with pregnancy success and embryonic survival at the molecular level. Such genes can be used in gene assisted selection programs to improve production and reproduction performance in cattle.

The following examples are intended to illustrate preferred embodiments of the invention and should not be interpreted to limit the scope of the invention as defined in the claims.

EXAMPLES

I. Association of Bovine FGF2 Gene with Milk Fat and Productive Life

Materials and Methods

Populations and Phenotypic Data The association between FGF2 and milk production and health traits was examined in a total of 2,167 individuals from 2 different Holstein cattle populations: the University of Wisconsin (UW) resource population, and the Cooperative Dairy DNA Repository (CDDR) population. For a detailed description of the UW populations see Gonda et al. (2006) and Khatib et al. (2007a). Yield deviation (YD) and predicted transmitting ability (PTA) data for the UW population and PTA data for the CDDR population for milk yield, milk protein and fat yields and percentages, productive life (PL), and somatic cell scores (SCS) were obtained from the Animal Improvement Programs Laboratory (Beltsville, Md.). A summary statistics of phenotypic data from the 2 resource populations is given in Table 1.

TABLE 1

Means and standard deviations (SD) of PTA of cows in the UW and of sons in CDDR resource populations for the production traits

|  | UW population (PTA) | | CDDR population (PTA) | |
|---|---|---|---|---|
| Trait | Mean (SD) | SD | Mean | SD |
| Fat, kg | −5.48 | 21.00 | 3.23 | 23.49 |
| Fat percentage | −0.0002 | 0.008 | −0.002 | 0.009 |
| Milk, kg | −142.69 | 540.56 | 110.71 | 741.26 |
| Protein yield, kg | −6.43 | 14.53 | 7.11 | 21.38 |
| Protein percentage | −0.008 | 0.003 | 0.001 | 0.004 |
| PL | 0.59 | 1.07 | −2.24 | 13.11 |
| SCS | 2.97 | 0.12 | 3.02 | 0.16 |

DNA Preparation, Polymorphism Detection, and Genotyping

A total of 851 blood samples were obtained from the UW resource population. Genomic DNA was extracted by using GFX Genomic Blood DNA Purification kit (Amersham Biosciences, Piscataway, N.J.). Semen samples from the CDDR population were obtained from 27 sires and their 1,316 sons, and genomic DNA was extracted by standard methods using proteinase K and phenol/chloroform.

In order to detect SNP in the FGF2 gene (GenBank Accession number NC_007304), 14 different sets of primers were designed (Table 2) to amplify a total of 6,389 bp (including all exons of the gene) using pooled DNA samples of 30 individuals. The PCR products were sequenced and SNP were identified by visually inspecting sequence traces.

TABLE 2

Primer sequences, locations, and product sizes

| Primer (Location) | Sequence | Fragment Size (bp) |
|---|---|---|
| FGF2-1 (5' UTR) | GAAAGCTCCGCAATGTAGAG (SEQ ID NO: 2) | 1076 |
| FGF2-2 (intron 1) | CCAACAAGGACCTTTTAGTTGG (SEQ ID NO: 3) | |
| FGF2-3 (intron 1) | GTTAACAAGGCCAAGTGGAGG (SEQ ID NO: 4) | 626 |
| FGF2-4 (intron 2) | CTGCCTCACACGAGCTGTC (SEQ ID NO: 5) | |
| FGF2-5 (intron 2) | CTGCTCTTCCAAGGAGATGTG (SEQ ID NO: 6) | 502 |
| FGF2-6 (3' UTR) | CCAAACTGAGCAGCTCACTG (SEQ ID NO: 7) | |
| FGF2-7 (3' UTR) | CAGTGAGCTGCTCAGTTTGG (SEQ ID NO: 8) | 749 |
| FGF2-8 (3' UTR) | CAGATCCCTCCTGAGTATTC (SEQ ID NO: 9) | |
| FGF2-In1 (intron 1) | TCAGTCTTCACATCCGTCTCAG (SEQ ID NO: 10) | 476 |
| FGF2-In2 (intron 1) | TCATACACTGAAGCCTGAAGC (SEQ ID NO: 11) | |
| FGF2-In3 (intron 1) | GAACCAGTCTGTTGTTCCGTGT (SEQ ID NO: 12) | 332 |
| FGF2-In4 (intron 1) | CAGATCAGATCAGATCAGTCGCT (SEQ ID NO: 13) | |
| FGF2-In5 (intron 1) | GCATCAGGTTTGAGGATCAA (SEQ ID NO: 14) | 490 |
| FGF2-In6 (intron 1) | AGGATCAAGTTTTCCACCTG (SEQ ID NO: 15) | |
| FGF2-In7 (intron 1) | TCACTCATGCCTGGAAGGGT (SEQ ID NO: 16) | 320 |
| FGF2-In8 (intron 1) | TATGTCCAGGTTGGCCTATAC (SEQ ID NO: 17) | |
| FGF2-In9 (intron 1) | AGAGTCTTTCTCTGAGTCAG (SEQ ID NO: 18) | 530 |
| FGF2-In10 (intron 1) | TGAAGTCATTTGGTGAAGGC (SEQ ID NO: 19) | |
| FGF2-In11 (intron 1) | CAGCAACTTAGCACTAGCTAC (SEQ ID NO: 20) | 390 |
| FGF2-In12 (intron 1) | CAGAGGCTCATTACATGGCC (SEQ ID NO: 21) | |
| FGF2-In13 (intron 1) | ATGGTCCAGCTCTCACATCC (SEQ ID NO: 22) | 472 |
| FGF2-In14 (intron 1) | GTGTAATATGTCTGAAACATC (SEQ ID NO: 23) | |
| FGF2-In15 (intron 1) | GCTGATACTGGTACATTACT (SEQ ID NO: 24) | 506 bp |
| FGF2-In16 (intron 1) | GCAAACAGTGGCTACCTTGG (SEQ ID NO: 25) | |
| FGF2-In17 (intron 2) | CCTGGTGGCTCAGATGGT (SEQ ID NO: 26) | 460 bp |
| FGF2-In18 (intron 2) | CTCAGAATTCTCATGCACT (SEQ ID NO: 27) | |

For individual genotyping, primers FGF2-F 5'-CATAGT-TCTGTAGACTAGAAG-3' (SEQ ID NO:28) and FGF2-R 5' CCTCTAAAGAAGGATTAAGT-CAAAATGGGGCTGGTA 3' (SEQ ID NO:29) were used to amplify a 207-bp fragment. The sequence of primer FGF2-R was modified to include a recognition site for the restriction enzyme Csp6I. Amplification was performed in a 25-μl reaction volume, which included 50 ng genomic DNA, 50 ng each primer, 200 μM each dNTP, 2.5 μl 10×PCR buffer (Promega, Madison, Wisc.), and 0.5 u Taq DNA polymerase (Promega). The temperature cycles were as follows: 95° C. for 5 min, followed by 32 cycles of 94° C. for 45 s, touchdown annealing from 63-50° C. for 45 s (−2° C./cycle), 72° C. for 45 s, and a final extension at 72° C. for 8 min. The PCR products were digested with the restriction enzyme Csp6I and electrophoresed on a 2.0% agarose gel. The A allele was indicated by a band of 207 bp, while the G allele was indicated by a band of 171 bp.

Statistical Analysis

Association of FGF2 variants with milk production and health traits was evaluated in 3 Holstein cattle populations. For the granddaughter-design CDDR population, PTAs for each trait were analyzed using the following allele substitution effect model:

$$y_{ij} = \mu + s_i + \beta x_{ij} + \epsilon_{ij}$$

where $y_{ij}$ represents the PTA of bull j of sire i; $\mu$ is a general constant; $s_i$ is the fixed effect of sire i; $\beta$ is the regression coefficient representing half the allele substitution effect ($\alpha/2$); $x_{ij}$ represents the number of allele G copies (0, 1, 2) at the FGF2 locus of bull j of sire i; and $\epsilon_{ij}$ represents the random residual term.

For the daughter-design UW population, dominance effects for individual cow PTAs and YDs for each trait were analyzed using the following mixed model:

$$y_{ijkl}=\mu+s_i+mgs_j+d_{ijk}\tau+f_l+\epsilon_{ijkl}$$

where $y_{ijkl}$ represents the PTA or YD for milk protein (kg and percentage), fat (kg and percentage), and productive life of daughter k of sire i of maternal grandsire j; $mgs_j$ represents the random effect for the maternal grand sire j; $\tau$ represents an effect associated with *M. paratuberculosis* infectious status; $d_{ijk}$ is an indicator variable assuming values 0 or 1 for noninfected and infected cows, respectively. *M. paratuberculosis* infection status was included in the model because the UW population was originally created to search for genetic markers associated with susceptibility to paratuberculosis; $f_l$ represents the effect of the FGF2 gene (l=AA, AG, GG); and the remaining terms were as defined in the previous model. While deviations for yield traits are corrected for the effect of contemporaries, individual measures of productive life do not account for these differences, therefore for this trait an additional random effect for herd was fitted in the analysis.

Additive genetic effect for the FGF2 locus on the individual records analysis was estimated as half of the difference between homozygous $(\hat{f}_{GG}-\hat{f}_{AA})/2$. Dominance effect was estimated as the difference between the heterozygote and the average of the two homozygotes. Complete dominance genetic effect was estimated as half of the difference between the heterozygote and recessive homozygote group $(\hat{f}_{AG}-\hat{f}_{AA})/2$.

All the analyses were implemented using the NLME library in R software v. 2.5.1, available form The R Foundation for Statistical Computing.

Results

Using the DNA sequencing approach, A/G SNP was detected; it is at position 11646 in intron 1 of FGF2. The frequencies of alleles A and G in the UW resource population were 0.35 and 0.65, respectively and the genotype frequencies (AA=0.13, AG=0.45, GG=0.42) were as expected for Hardy-Weinberg equilibrium. The frequency of allele G in the CDDR population was 0.63. The association between the FGF2 SNP and milk production and health traits was examined in 851 cows from the UW population, and in 1,316 bulls from the CDDR population.

Table 3 shows the estimates of the additive, dominance, and complete dominance for PTA of milk production and productive life traits in the UW population. Complete dominant gene action was significant for fat yield, fat percentage, and productive life. A dominance genetic effect was significant for fat yield and fat percentage. For YD, complete dominant gene action was significant for fat yield (P<0.05) and productive life (P<0.01) with estimates of 9.27±3.77 kg and 1.54±0.56 mo respectively. An additive genetic effect was significant only for productive life (P<0.05), with an estimate of 1.22±0.57 mo. For fat yield, the least-squares estimate of the AA genotype was 13.83 vs. 31.96 and 26.14 kg for the AG and GG genotypes, respectively. Similarly, for productive life, the AG and GG genotypes showed an increase of 3.1 and 2.46 mo respectively compared to the AA genotype.

For the CDDR population, analysis of PTAs for milk yield and composition and productive life did not reveal significant associations with any of the examined traits (Table 4). However, the directions of least-squares estimates for fat yield were consistent with those in the UW population. The estimate of genotype AA was 5.59 vs. 6.77 kg fat for genotype GG.

TABLE 3

Least-squares means (LSM) for FGF2 genotypes and estimates of additive, dominance, and complete dominance effects for milk yield and composition traits and for productive life estimated from PTAs in the UW population

| Trait | LSM AA | LSM AG | LSM GG | Additive effect | Dominance effect | Complete dominance |
|---|---|---|---|---|---|---|
| Fat yield | −7.46 | −2.91 | −4.49 | 1.48 ± 1.12 | 3.06 ± 1.43* | 2.27 ± 1.06* |
| Fat percentage | −1.20 | 0.71 | 0.48 | 0.84 ± 0.40* | 1.07 ± 0.51* | 0.95 ± 0.38* |
| Milk yield | −108.71 | −122.25 | −150.26 | −20.77 ± 29.57 | 7.23 ± 37.60 | −6.77 ± 27.97 |
| Protein yield | −5.88 | −5.36 | −6.57 | −0.34 ± 0.79 | 0.85 ± 1.00 | 0.25 ± 0.74 |
| Protein Percentage | −0.93 | −0.60 | −0.75 | 0.09 ± 0.19 | 0.24 ± 0.24 | 0.16 ± 0.18 |
| PL | 0.34 | 0.49 | 0.49 | 0.07 ± 0.03† | 0.08 ± 0.05 | 0.07 ± 0.03* |

†P < 0.1;
*P < 0.05

TABLE 4

Least-squares means (LSM) for FGF2 genotypes and estimates of additive, dominance, and complete dominance effects for milk yield and composition traits and for productive life estimated from PTAs in the CDDR population

| Trait | LSM AA | LSM AG | LSM GG | Additive effect | Dominance effect | Complete dominance |
|---|---|---|---|---|---|---|
| Fat yield | 5.59 | 5.33 | 6.77 | 0.59 ± 0.98 | −0.85 ± 1.18 | −0.13 ± 0.87 |
| Fat percentage | −0.010 | 0.009 | −0.030 | 0.050 ± 0.040 | −0.001 ± 0.040 | 0.020 ± 0.030 |
| Milk yield | 268.24 | 223.60 | 220.52 | −23.85 ± 25.50 | −20.77 ± 31.95 | −22.31 ± 23.48 |
| Protein yield | 11.97 | 11.19 | 11.43 | −0.26 ± 0.67 | −0.50 ± 0.81 | −0.38 ± 0.60 |

TABLE 4-continued

Least-squares means (LSM) for FGF2 genotypes and estimates of additive, dominance, and complete dominance effects for milk yield and composition traits and for productive life estimated from PTAs in the CDDR population

| Trait | LSM AA | LSM AG | LSM GG | Additive effect | Dominance effect | Complete dominance |
|---|---|---|---|---|---|---|
| Protein Percentage | 0.015 | 0.017 | 0.019 | 0.018 ± 0.010 | 0.003 ± 0.020 | 0.010 ± 0.010 |
| PL | −0.4 | −0.38 | −0.42 | 0.19 ± 0.55 | 0.59 ± 0.37 | 0.39 ± 0.49 |

Discussion

Using the pooled DNA sequencing approach to search for polymorphisms in 6,389 bp including 466 bp of the 3 three exons of the gene, SNP in intron 1 was identified at position 11646. It is widely accepted that highly conserved sequences are less subject to mutations. For example, investigation of 481 segments that are absolutely conserved between orthologous regions of the human, rat and mouse genomes revealed almost no natural variation in the human population and only 6 variants were found in a total of 106,767 bases examined (Bejerano et al., 2004). Indeed, there is a similarity of 97% among bovine, mouse, and human for the protein sequence of FGF2.

The SNP in FGF2 was investigated for association with production traits in 2 Holstein populations, and significant associations between FGF2 variants and fat yield and percentage, SCS, and productive life traits were observed in the UW but not in the CDDR population. However, the correlation between SCS and productive life in the North America Holstein population is −0.36 (Khatib et al., 2005). Both SCS and productive life are indicators of health conditions in cows. Productive life is a longevity trait defined as a cow's total lifetime months in milk with limits of 10 months per lactation and 7 years of age (VanRaden and Wiggans, 1995). The association of FGF2 with milk composition and health traits was consistent in the examined populations.

In a previous study, we reported a significant association between the protease inhibitor gene (PI) and productive life and milk composition traits in Holstein dairy cattle (Khatib et al., 2005). In a subsequent study aimed at investigating the PI region, we reported the association of the UTMP gene—located on bovine chromosome 21 within 321.6 kb of PI—with productive life in both the CDDR and the UW populations (Khatib et al., 2007a). We concluded that additional studies are needed to confirm whether the observed associations between PI and UTMP with productive life were due to polymorphisms in these genes or to other loci in that region. In this study, we found that FGF2, which is a member of the same pathway as UTMP, was also associated with a significant increase in productive life.

This is the first report on the association between FGF2 and production traits in dairy cattle. However, it remains to be investigated by which mechanisms FGF2 affects these traits. For milk composition traits, it has been reported that FGF2 is expressed in the mammary gland and plays a role in local regulation of mammary development in mouse (Coleman-Krnacik and Rosen, 1994) and in cattle (Plath et al., 1998). In addition, FGF2 has been reported to stimulate IFNT expression (Michael et al., 2006), which in turn actives a cascade of genes previously found to be associated with milk production and health traits.

Bovine IFNT is released by the conceptus as early as Day 9 of pregnancy and serves as the signal for maternal recognition of pregnancy. IFNT binds to the receptor IFNAR present on the cells of the endometrium and activates the phosphorylation of janus-kinases JAK1 and TYK2, which in turn phosphorylate the tyrosine residues of STAT1 and STAT2. Following phosphorylation, both STAT1 and STAT2 are released from the receptor and bind a third DNA-binding protein, interferon regulatory factor (IRF) 9, to form the ISGF3 complex. Then, the ISGF3 complex translocates from the cytoplasm to the nucleus and binds to the promoter region of IRF1 to increase the rate of transcription of targeted genes such as STAT1, STAT2, IRF9, and 2', 5' oligoadenylate synthetase (OAS). Expression of OAS may enhance the secretion of UTMP and OPN proteins (Spencer and Bazer, 2002; Stewart et al., 2002). The expression of UTMP is also induced by STAT5 which is stimulated by the growth hormone receptor (GHR) (Spencer and Bazer, 2002; Stewart et al., 2002; Spencer and Bazer, 2004). Several members of this pathway, including STAT1 (Cobanoglu et al., 2006), UTMP (Khatib et al., 2007a), OPN (Leonard et al., 2005), STAT5 (Khatib et al., 2008), and GHR (Blott et al., 2003), have been reported to be associated with milk production and health traits. Taken together, our findings support the usefulness of the candidate pathway strategy in choosing candidate genes affecting quantitative traits.

II. Association of FGF2 SNP11646 with Embryonic Mortality in Cattle

Materials and Methods

Embryo Data Collection

A total of 281 independent ovaries were collected from a total of 281 cows from a local abattoir over a period of 26 months and used in in vitro fertilization (IVF) experiments with semen from 7 sires. On average, 12 oocytes were aspirated from each ovary. Oocytes from 191 ovaries were fertilized with semen from one of three sires (i.e., semen from a particular sire was used to fertilize all oocytes harvested from one ovary). For the remaining 90 ovaries, aspirated oocytes were divided into 2 groups; each group was fertilized with semen from one of 4 additional sires. A summary of the experimental design including the number of oocytes used in the IVF for each sire is reported in Table 5.

TABLE 5

Number of ovaries and oocytes used in in-vitro fertilization with each sire and average number of oocytes aspirated from each cow

| Sire | Number of ovaries | Total oocytes fertilized | Average number of oocytes/ovary (std dev) |
|---|---|---|---|
| 1 | 91 | 1217 | 13.37 (9.08) |
| 2 | 62 | 1140 | 18.39 (16.21) |
| 3 | 38 | 518 | 13.63 (7.43) |
| 4 | 61[a] | 506 | 8.30 (5.11) |
| 5 | 61[a] | 515 | 8.44 (4.57) |

TABLE 5-continued

Number of ovaries and oocytes used in in-vitro fertilization with each sire and average number of oocytes aspirated from each cow

| Sire | Number of ovaries | Total oocytes fertilized | Average number of oocytes/ovary (std dev) |
|---|---|---|---|
| 6 | 29[b] | 318 | 10.97 (5.80) |
| 7 | 29[b] | 328 | 11.31 (5.81) |
| Total | 281 | 4542 | 12.24 (9.68) |

[a,b]Oocytes were aspirated from each of 61 and 29 ovaries, respectively, divided into two groups, and fertilized in parallel with semen from 2 different sires.

Oocytes were aspirated from antral follicles; processed in TALP-Hepes with 0.22 mM sodium pyruvate, 25 μg/ml gentamicin sulfate, and 3 mg/ml BSA; and immediately incubated for 20-24 h in 50-μl drops of maturation medium that had been equilibrated in 5% carbon dioxide in air at 39° C. and high humidity. On Day 2 oocytes were washed 3× in TALP-Hepes and then were placed (up to 10 oocytes each) in 44-μl mineral oil-overlaid microdrops of IVF-Talp (Biowhittaker, Walkersburg, Md.) supplemented with 0.22 mM sodium pyruvate, 25 μg/ml gentamicin sulfate, and 6 mg/ml essentially fatty acid free BSA.

Oocytes were fertilized with frozen-thawed percoll-separated bull semen after being adjusted to a final concentration of 1 million sperm/ml. Each microdrop received 2.0 μg/ml heparin to help induce capacitation; hypotaurine, penicillamine, and epinephrine also added were to maintain sperm membrane integrity and motility. After fertilization, putative zygotes were stripped of their cumulus cells by vortexing for 3 minutes, then washed 3× in TALP-Hepes before being placed into 50 μl mineral oil-overlaid microdrops of synthetic oviductal fluid (Biowhittaker) supplemented with 0.22 mM sodium pyruvate, 25 μg/ml gentamicin sulfate, and 8 mg/ml essentially fatty acid free BSA.

Survival and Fertilization Rates

A total of 4542 fertilizations were performed. Survival rate of embryos was calculated as the number of viable embryos out of the number of total cultured embryos evaluated at Day 7 of development (fertilization=day 0). Viability was determined as a function of the embryo's ability to attain the morphological stage of blastocyst on Day 7 of development. Embryos that failed to show cellular compaction (morula stage) on day 5 or 6 were considered non viable. Therefore only embryos exhibiting adequate compaction followed by the formation of a blastocoele on Day 7 were considered viable. Fertilization rate was calculated as the number of embryos produced out of the total number of fertilizations. Survival and fertilization rates were assessed under the same environmental conditions to minimize biased conclusions. The environmental conditions during incubation were: temperature of 39° C., 5% carbon dioxide in compressed air (~20% oxygen tension), and 95% relative humidity in a water jacketed $CO_2$ incubator.

Polymorphism Identification and Genotyping

We extended our SNP search to include the 5' UTR of FGF2 using the primers FGF1-F 5'-GACCTATTAGATGT-GACGCC-3' (SEQ ID NO:30) and FGF1-R 5'-GGACTG-GCTTTGCTGAGCAG-3' (SEQ ID NO:31). A G/T SNP was identified at position 23 (SNP23) of FGF2 (GenBank Accession number NC_007304). For individual genotyping of SNP11646, primers FGF2-F 5'-CATAGTTCTGTAGACTA-GAAG-3' (SEQ ID NO:28) and FGF2-R 5'-CCTCTAAA-GAAGGATTAAGTCAAAATGGGGCTGGTA-3' (SEQ ID NO:29) were used to amplify a 207-bp fragment. For genotyping SNP23, primers FGF1-F and FGF1-R were used to amplify a 790-bp fragment. Amplification was performed in a 25-μl reaction volume, which included 50 ng genomic DNA, 50 ng each primer, 200 μM each dNTP, 2.5 μl 10× PCR buffer (Promega, Madison, Wisc.), and 0.5 u Taq DNA polymerase (Promega). The temperature cycles were as follows: 95° C. for 5 min, followed by 32 cycles of 94° C. for 45 s, touchdown annealing from 63 to 50° C. for 45 s (−2° C./cycle), 72° C. for 45 s, and a final extension at 72° C. for 8 min. To detect variants of SNP11646 and SNP23, PCR products were digested with the restriction enzymes Csp6I and HaeII, respectively, and electrophoresed on a 2.0% agarose gel. The A and G alleles of SNP11646 were indicated by bands of 207 and 171 bp, respectively, the G allele of SNP23 was indicated by a band of 425 bp, and the T allele was indicated by bands of 285 and 140 bp.

Statistical Analysis

No evidence of linkage disequilibrium was found between SNP23 and SNP11646, therefore they were assumed independent in the subsequent analysis. Ovaries from which fewer than 5 eggs were harvested were discarded and not further analyzed. Association between FGF2 polymorphisms and proportion of fertilized ova (fertilization rate) and survival of fertilized ova at Day 7 (survival rate) was analyzed using the following mixed linear model:

$$y_{ijk} = \mu + o_i + s_j + SNP11646_{ijk} + SNP23_{ijk} + \epsilon_{ijk}$$

where $y_{ijk}$ represents in turn, the survival or fertilization rate of a batch of ova k from ovary i fertilized with semen from sire j; $\mu$ represents the mean for the trait considered; $o_i$ represents the random effect of the individual ovary from which ova were harvested; $s_j$ represents the random effect of sire; $SNP11646_{ijk}$ represents the fixed effect of SNP11646 genotype (AA, AG, GG); $SNP23_{ijk}$ represents the fixed effect of SNP23 genotype (GG, GT, TT); and $\epsilon_{ijk}$ represent the residuals, assumed normal and independent. Ovary effect was fitted to account for the experimental design in which, for some ovaries, oocytes collected were fertilized with different sires. Ovaries and sires were assumed uncorrelated in the analysis, with variance structures $I\sigma^2_o$ and $I\sigma^2_s$ respectively. An interaction effect between the two polymorphisms included in a preliminary analysis did not reach significance and was excluded from the final model. For both SNP, additivity and dominance were tested as the difference between the two homozygous genotypes (additive) and the difference between the heterozygous and the average of the two homozygous genotypes (dominance). Additive and dominance effects were calculated as the weighted difference between the two alternative homozygous genotypes (i.e., ½(GG−AA); ½(GG−TT)), or the difference between the heterozygous and the average of the two homozygous genotypes (i.e., AG−½ (AA+GG); GT−½ (GG+TT)). All the analyses were performed with the function lmer of the lme4 package of R software v. 2.5.1.

Results

In this study we extended our search for SNP in the 5' UTR of FGF2 and identified a G/T SNP at position 23. To investigate the association of SNP23 and SNP11646 with fertility traits, we performed a total 4,542 in vitro fertilizations using semen from 7 sires and ovaries from 281 cows which produced a total of 3,171 embryos. Survival and fertilization rates were evaluated at Day 7 of development.

Genotyping results of the cows revealed that the frequencies of the G and A alleles at SNP11646 were 0.53 and 0.47, respectively, while frequencies of the G and T alleles at SNP23 were 0.82 and 0.18, respectively. Table 6 shows the estimated differences between genotypes of cows for SNP11646 and SNP23 for survival and fertilization rates. For fertilization rate, no significant genotypic differences were found for either SNP. On the contrary, embryonic survival showed a significant association with SNP11646. Survival rate of embryos produced from GG dams was 10.73% higher than that of embryos produced from AG dams (P=0.005) and 8.66% higher than that of embryos produced from AA dams (P=0.079). Dominance test was significant for this SNP (P=0.047) and estimates of additive and dominance genetic effects for survival rate were of 4.5% (±0.023) and 6.3% (±0.031), respectively. Least square means and standard errors for survival and fertilization rates for the cows' genotypes for SNP11646 and SNP23 are shown in Table 7. Table 8 shows survival and fertilization rates and the total number of embryos produced from cows of each genotype for each sire. The GG genotype was associated with an increase in survival rate compared to the AG and AA genotypes. The highest difference in survival rate among genotypes was observed for embryos produced from Sire 5 with 59% survival rate for GG cows vs. 28% survival rate for AA cows. Sires 1, 2, 3, 4, and 6 showed genotype differences of 8% to 10% survival rate. In contrast, for sire 7, survival rates of embryos produced form AA and GG cows were not significantly different.

TABLE 6

Estimated differences expressed in percentages (±standard error) between dams' genotypes for SNP11646 and SNP23 for survival and fertilization rates

| Trait | SNP11646 | | | SNP23 | | |
| --- | --- | --- | --- | --- | --- | --- |
| | GG-AG | GG-AA | AG-AA | GG-GT | GG-TT | GT-TT |
| Survival rate (%) | 10.7[b] ± 3.7 | 8.6[a] ± 4.9 | −2.1 ± 4.7 | 3.3 ± 3.0 | 7.0 ± 9.4 | 4.28 ± 9.7 |
| Fertilization rate (%) | −4.0 ± 3.0 | 2.5 ± 4.0 | −7.6 ± 4.0 | 1.9 ± 3.2 | 3.4 ± 7.4 | 2.0 ± 7.6 |

[a]P = 0.079 for the difference in survival rate between the GG and AA genotypes
[b]P = 0.005 for the difference in survival rate between the GG and AG genotypes

TABLE 7

Least square means and standard errors for embryo survival and fertilization rates for each cow genotype for SNP11646 and SNP23

| Trait | SNP11646 | | | SNP23 | | |
| --- | --- | --- | --- | --- | --- | --- |
| | AA | AG | GG | GG | GT | TT |
| Survival rate | 0.28 ± 0.039 | 0.26 ± 0.041 | 0.36 ± 0.046 | 0.33 ± 0.022 | 0.30 ± 0.034 | 0.26 ± 0.092 |
| Fertilization rate | 0.65 ± 0.031 | 0.72 ± 0.033 | 0.68 ± 0.037 | 0.70 ± 0.018 | 0.68 ± 0.033 | 0.67 ± 0.037 |

TABLE 8

Survival and fertilization rates (%) for each cow SNP11646 genotype and the total number of embryos and fertilizations for each sire

| | Survival rate (%) | | | | Fertilization rate (%) | | | |
| --- | --- | --- | --- | --- | --- | --- | --- | --- |
| | cows' genotype[a] | | | | | | | |
| Sire | AA | AG | GG | Total embryos | AA | AG | GG | Total fertilizations |
| Sire 1 | 40 | 39 | 48 | 240 | 76 | 77 | 72 | 318 |
| Sire 2 | 32 | 33 | 41 | 336 | 50 | 72 | 79 | 518 |
| Sire 3 | 26 | 26 | 36 | 368 | 71 | 70 | 75 | 506 |
| Sire 4 | 24 | 30 | 34 | 372 | 71 | 78 | 67 | 515 |
| Sire 5 | 28 | 24 | 59 | 239 | 72 | 73 | 74 | 328 |
| Sire 6 | 33 | 34 | 43 | 805 | 72 | 66 | 75 | 1140 |
| Sire 7 | 36 | 30 | 34 | 811 | 70 | 65 | 66 | 1217 |

[a]Numbers of cows with AA, AG, and GG genotypes were 70, 123, and 88 respectively.

REFERENCES CITED

Bejerano, G., M. Pheasant, I. Makunin, S. Stephen, W. J. Kent, J. S. Mattick, and D. Haussler. 2004. Ultraconserved elements in the human genome. Science 304:1321-1325.

Blott, S., J. J. Kim, S. Moisio, A. Schmidt-Küntzel, A. Cornet, P. Berzi, N. Cambisano, C. Ford, G. Grisart, D. Johnson, L. Karim, P. Simon, R. Snell, R. Spelman, J. Wong, J. Vilkki, M. Georges, F. Farnir, and W. Coppieters. 2003. Molecular dissection of a quantitative trait locus: a phenylalanine-to-tyrosine substitution in the transmembrane domain of the bovine growth hormone receptor is associated with a major effect on milk yield and composition. Genetics 163:253-66.

Butler, W. R., and R. D. Smith. 1989. Interrelationships between energy balance and postpartum reproductive function in dairy cattle. J. Dairy Sci. 72:767-783.

Carlone, D. L., and V. Rider. 1993. Embryonic modulation of basic fibroblast growth factor in the rat uterus. Biol. Reprod. 49:653-665.

Cobanoglu, O., I. Zaitoun, Y. M. Chang, G. E. Shook, and H. Khatib. 2006. Effects of the signal transducer and activator of transcription 1 (STAT1) gene on milk production traits in Holstein dairy cattle. J. Dairy Sci. 89:4433-4437.Khatib, H., V. Schutzkus, Y. M. Chang and G. J. M. Rosa. 2007a. Pattern of expression of the uterine milk protein gene and its association with productive life in dairy cattle. J. Dairy Sci. 90:2427-2433.

Cobanoglu, O., I. Zaitoun, Y. M. Chang, G. E. Shook, and H. Khatib. 2006. Effects of the signal transducer and activator of transcription 1 (STAT1) gene on milk production traits in Holstein dairy cattle. J. Dairy Sci. 89:4433-4437.

Coleman-Krnacik, S., and J. M. Rosen. 1994. Differential temporal and spatial gene expression of fibroblast growth factor family members during mouse mammary gland development. Mol. Endocrinol. 8:218-29.

Gonda, M. G., Y. M. Chang, G. E. Shook, M. T. Collins and B. W. Kirkpatrick. 2006. Genetic variation of *Mycobacterium avium* ssp. paratuberculosis infection in US Holsteins. J. Dairy Sci. 89:1804-1812.

Khatib, H., E. Heifetz, and J. C. Dekkers. 2005. Association of the protease inhibitor gene with production traits in Holstein dairy cattle. J. Dairy Sci. 88:1208-1213.

Khatib, H., V. Schutzkus, Y. M. Chang and G. J. M. Rosa. 2007a. Pattern of expression of the uterine milk protein gene and its association with productive life in dairy cattle. J. Dairy Sci. 90:2427-2433.

Khatib, H., I. Zaitoun, J. Wiebelhaus-Finger, Y. M. Chang and G. J. M. Rosa. 2007. The association of bovine PPARGC1A and OPN genes with milk composition in two independent Holstein cattle populations. J. Dairy Sci. 90:2966-2970.

Khatib, H., R. L. Monson, V. Schutzkus, D. M. Kohl, G. J. M. Rosa, and J. J. Rutledge. 2008. Mutations in the STAT5A Gene are Associated with Embryonic Survival and Milk Composition in Cattle. J. Dairy Sci. (in press).

Khatib, H., R. L. Monson, V. Schutzkus, D. M. Kohl, G. J. M. Rosa, and J. J. Rutledge. 2008. Mutations in the STAT5A gene are associated with embryonic survival and milk composition in cattle. J. Dairy Sci. 91:784-793.

Khatkar, M. S, P. C. Thomson, I. Tammen, H. W. Raadsma. 2004. Quantitative trait loci mapping in dairy cattle: review and meta-analysis. Genet Sel Evol. 36:163-190.

Larson, R. C., G. G. Ignotz, and W. B. Currie. 1992. Transforming growth factor beta and basic fibroblast growth factor synergistically promote early bovine embryo development during the fourth cell cycle. Mol. Reprod. Dev. 33:432-435.

Leonard, S., H. Khatib, V. Schutzkus, Y. M. Chang, and C. Maltecca. 2005. Effects of the osteopontin gene variants on milk production traits in dairy cattle. J. Dairy Sci. 88:4083-4086.

Lucy, M. C. 2001. Reproductive loss in high-producing dairy cattle: where will it end? J. Dairy Sci. 84:1277-1293.

Martal, J., N. Chêne, S. Camous, L. Huynh, F. Lantier, P. Hermier, R. L'Haridon, G. Charpigny, M. Charlier, and G. Chaouat. 1997. Recent developments and potentialities for reducing embryo mortality in ruminants: the role of IFN-tau and other cytokines in early pregnancy. Reprod. Fertil. Dev. 9:355-380. Michael, D. D., I. M. Alvarex, O. M. Ocón, A. M. Powell, N. C. Talbot, S. E. Johnson, and A. D. Ealy. 2006. Fibroblast growth factor-2 is expressed by the bovine uterus and stimulates interferon-tau production in bovine trophectoderm. Endocrinology 147: 3571-3579.

Michael, D. D., I. M. Alvarex, O. M. Ocón, A. M. Powell, N. C. Talbot, S. E. Johnson, and A. D. Ealy. 2006. Fibroblast growth factor-2 is expressed by the bovine uterus and stimulates interferon-tau production in bovine trophectoderm. Endocrinology 147: 3571-3579.

Moore, K., and W. W. Thatcher. 2006. Major advances associated with reproduction in dairy cattle. J. Dairy Sci. 89:1254-1266.

Ocón-Grove, O. M., F. N. Cooke, I. M. Alvarez, S. E. Johnson, T. L. Ott, and A. D. Ealy AD. 2007. Ovine endometrial expression of fibroblast growth factor (FGF) 2 and conceptus expression of FGF receptors during early pregnancy. Domest. Anim. Endocrinol. (In press).

Plath, A., R. Einspanier, C. Gabler, F. Peters, F. Sinowatz, D. Gospodarowicz, D. Schams. 1998. Expression and localization of members of the fibroblast growth factor family in the bovine mammary gland. J. Dairy Sci. 81:2604-2613.

Rothschild, M. F., and M. Soller. 1997. Candidate gene analysis to detect genes controlling traits of economic importance in domestic livestock. Probe 8:13-22.

Spencer, T. E., and F. W. Bazer. 2002. Biology of progesterone action during pregnancy recognition and maintenance of pregnancy. Front. Biosci. 1:d1879-1898.

Spencer, T. E., and F. W. Bazer. 2004. Conceptus signals for establishment and maintenance of pregnancy. Reprod. Biol Endocrinol. 2:49.

Stewart, M. D., Y. Choi, G. A. Johnson, L. Y. Yu-Lee, F. W. Bazer and T. E. Spencer. 2002. Roles of Stat1, Stat2, and interferon regulatory factor-9 (IRF-9) in interferon tau regulation of IRF-1. Biol. Reprod. 66:393-400.

VanRaden, P. M., and G. R. Wiggans. 1995. Productive life evaluations: calculation, accuracy, and economic value. J. Dairy Sci. 78:631-638.

VanRaden, P. M. and R. H. Miller. 2006. Effects of nonadditive genetic interactions, inbreeding, and recessive defects on embryo and fetal loss by seventy days. J. Dairy Sci. 89:2716-2721.

Veerkamp, R. F., and B. Beerda. 2007. Genetics and genomics to improve fertility in high producing dairy cows. Theriogenology 68S:S266-S273.

Royal, M., G. E. Mann, and A. P. Flint. 2000. Strategies for reversing the trend towards subfertility in dairy cattle. Vet. J. 160:53-60. Shook, G. E. 2006. Major advances in determining appropriate selection goals. J. Dairy Sci. 89:1349-1361.

Spencer, T. E., and F. W. Bazer. 2004. Conceptus signals for establishment and maintenance of pregnancy. Reprod. Biol Endocrinol. 2:49.

What is claimed is:

1. A method for detecting a single nucleotide polymorphism in the bovine FGF2 gene, wherein the FGF2 gene comprises SEQ ID NO: 1, the method comprising:
   detecting, in a nucleic acid sample from a bovine, the presence of a G nucleotide in intron 1 of the FGF2 gene at the position corresponding to position 1326 of SEQ ID NO: 1.

2. A method for genotyping a bovine cell, comprising obtaining a nucleic acid sample from said cell and detecting the presence of a G nucleotide in intron 1 of the FGF2 gene at the position corresponding to position 1326 of SEQ ID NO: 1.

3. The method of claim 2, wherein the bovine cell is an adult cell, an embryo cell, a sperm, an egg, a fertilized egg, or a zygote.

4. The method of claim 2, wherein the G nucleotide is detected by sequencing the FGF2 gene, or a fragment thereof, isolated from the cell.

5. The method of claim 4, wherein the gene or a fragment thereof is isolated from the cell via amplification by polymerase chain reaction (PCR) of genomic DNA of the cell, or by RT-PCR of suitable mRNA of the cell.

6. The method of claim 4, wherein both copies of the FGF2 gene in the cell are genotyped.

7. A method for progeny testing of cattle, the method comprising collecting a nucleic acid sample from said progeny, and genotyping said nucleic sample according to the method of claim 2.

8. A method for selectively breeding of cattle using a multiple ovulation and embryo transfer (MOET) procedure, the method comprising superovulating a female bovine animal, collecting eggs from said superovulated female, in vitro fertilizing said eggs using sperm from a suitable male animal, implanting said fertilized eggs into other females allowing for an embryo to develop, and genotyping said developing embryo according to the method of claim 2, and terminating pregnancy if the developing embryo does not have a G nucleotide in intron 1 of the FGF2 gene at the position corresponding to position 1326 of SEQ ID NO: 1.

9. A method for selectively breeding dairy cattle, comprising selecting a bull that is homozygous for the presence of a G nucleotide in intron 1 of the FGF2 gene at a position corresponding to position 1326 of SEQ ID NO: 1 and using its semen for fertilizing a female animal.

10. The method of claim 9, wherein the female animal is in vitro fertilized.

11. The method of claim 9, wherein said female animal is homozygous for the presence of a G nucleotide in intron 1 of the FGF2 gene at a position corresponding to position 1326 of SEQ ID NO: 1.

12. A method for identifying a dairy cattle as having an increased embryo survival rate, said method comprising:
   detecting in a nucleic acid sample from said cattle the presence of a G nucleotide in intron 1 of the both copies of the FGF2 gene at the position corresponding to position 1326 of SEQ ID NO: 1;
   wherein the presence of a G nucleotide in intron 1 of the both copies of the FGF2 gene at the position corresponding to position 1326 of SEQ ID NO: 1 is indicative of an increased embryo survival rate.

* * * * *

UNITED STATES PATENT AND TRADEMARK OFFICE
CERTIFICATE OF CORRECTION

PATENT NO. : 8,067,171 B2
APPLICATION NO. : 12/424796
DATED : November 29, 2011
INVENTOR(S) : Hasan Khatib It is certified that error appears in the above-identified patent and that said Letters Patent is hereby corrected as shown below:

Title Page, Inventor should read:
-- (75) Inventor: Hasan Khatib, Madison, WI (US) --.

Signed and Sealed this
Seventeenth Day of January, 2012

David J. Kappos
*Director of the United States Patent and Trademark Office*